United States Patent
Djupesland et al.

(10) Patent No.: US 10,639,438 B2
(45) Date of Patent: May 5, 2020

(54) DELIVERY DEVICES

(71) Applicant: OptiNose AS, Oslo (NO)

(72) Inventors: Per Gisle Djupesland, Oslo (NO); Erik Andreassen, Oslo (NO); Rune Harald Gaarder, Oslo (NO); Christophe Péricé, Toulon (FR); Andreas Nilsson, Oslo (NO)

(73) Assignee: OptiNose AS, Oslo (NO)

( * ) Notice: Subject to any disclaimer, the term of this patent is extended or adjusted under 35 U.S.C. 154(b) by 222 days.

(21) Appl. No.: 15/936,251

(22) Filed: Mar. 26, 2018

(65) Prior Publication Data

US 2019/0099565 A1    Apr. 4, 2019

Related U.S. Application Data

(63) Continuation of application No. 15/133,356, filed on Apr. 20, 2016, now abandoned, which is a
(Continued)

(30) Foreign Application Priority Data

Nov. 28, 2006  (GB) .................................. 0623731.7

(51) Int. Cl.
*A61M 15/00* (2006.01)
*A61M 11/00* (2006.01)
(Continued)

(52) U.S. Cl.
CPC ...... *A61M 15/0098* (2014.02); *A61M 11/006* (2014.02); *A61M 11/06* (2013.01);
(Continued)

(58) Field of Classification Search
CPC .. A61M 11/00; A61M 11/006; A61M 11/007; A61M 11/02; A61M 11/06;
(Continued)

(56) References Cited

U.S. PATENT DOCUMENTS

| 605,436 A | 6/1898 | Kellogg |
|---|---|---|
| 642,748 A | 2/1900 | Manners |

(Continued)

FOREIGN PATENT DOCUMENTS

| GB | 2 381 460 | 5/2003 |
|---|---|---|
| GB | 2 404 867 | 2/2005 |

(Continued)

OTHER PUBLICATIONS

Cindy H. Dubin, *Nothing to Sneeze At*, Pharmaceutical Formulation & Quality Magazine (Jan. 29, 2003).
(Continued)

*Primary Examiner* — Colin W Stuart
(74) *Attorney, Agent, or Firm* — Finnegan, Henderson, Farabow, Garrett & Dunner LLP

(57) ABSTRACT

A delivery device for delivering a metered amount of substance (L) in response to exhalation by a user, the delivery device comprising: a mouthpiece (5) through which the user in use exhales; an outlet (45) from which substance is delivered; and a dispensing unit (35) which is operable to dispense a metered amount of substance through the outlet in response to exhalation by the user through the mouthpiece, wherein the dispensing unit comprises a body member (37) which includes a cavity (39) for containing a metered amount of substance, an outlet nozzle (43) which is fluidly connected to the cavity from which substance is in use delivered, and a dispensing (41) member which is movably disposed in the cavity and configured to be driven through the cavity by a driving pressure created by exhalation of the user, such as to cause substance to be delivered from the outlet nozzle.

23 Claims, 4 Drawing Sheets

Related U.S. Application Data continuation of application No. 14/171,554, filed on Feb. 3, 2014, now abandoned, which is a continuation of application No. 12/516,401, filed as application No. PCT/IB2007/004353 on Nov. 28, 2007, now abandoned.

(51) Int. Cl.
*A61M 15/08* (2006.01)
*A61M 11/06* (2006.01)

(52) U.S. Cl.
CPC ...... *A61M 15/002* (2014.02); *A61M 15/0008* (2014.02); *A61M 15/009* (2013.01); *A61M 15/0021* (2014.02); *A61M 15/0028* (2013.01); *A61M 15/0031* (2014.02); *A61M 15/0086* (2013.01); *A61M 15/0091* (2013.01); *A61M 15/08* (2013.01); *A61M 2202/04* (2013.01)

(58) Field of Classification Search
CPC ...... A61M 11/08; A61M 13/00; A61M 15/00; A61M 15/0091; A61M 15/0098; A61M 15/08; A61M 15/0086; A61M 15/002; A61M 15/0021; A61M 15/0028; A61M 2202/04
See application file for complete search history.

(56) References Cited

U.S. PATENT DOCUMENTS

| | | |
|---|---|---|
| 658,436 A | 9/1900 | Groth |
| 746,749 A | 12/1903 | Seidel |
| 794,641 A | 7/1905 | Ramey |
| 902,832 A | 11/1908 | Philbrook |
| 4,820,306 A | 4/1989 | Gorman et al. |
| 5,797,392 A | 8/1998 | Keldmann et al. |
| 6,648,848 B1 | 11/2003 | Keldmann et al. |
| 6,715,485 B1 | 4/2004 | Djupesland |
| D530,815 S | 10/2006 | Murphy et al. |
| 7,347,201 B2 | 3/2008 | Djupesland |
| 7,377,901 B2 | 5/2008 | Djupesland et al. |
| 7,481,218 B2 | 1/2009 | Djupesland |
| 7,543,581 B2 | 6/2009 | Djupesland |
| 7,740,014 B2 | 6/2010 | Djupesland |
| 7,784,460 B2 | 8/2010 | Djupesland et al. |
| 7,841,337 B2 | 11/2010 | Djupesland |
| 7,854,227 B2 | 12/2010 | Djupesland |
| 7,934,503 B2 | 5/2011 | Djupesland et al. |
| 7,975,690 B2 | 7/2011 | Djupesland |
| 8,047,202 B2 | 11/2011 | Djupesland |
| 8,146,589 B2 | 4/2012 | Djupesland |
| 8,171,929 B2 | 5/2012 | Djupesland et al. |
| 8,327,844 B2 | 12/2012 | Djupesland |
| 8,511,303 B2 | 8/2013 | Djupesland |
| 8,522,778 B2 | 9/2013 | Djupesland |
| 8,550,073 B2 | 10/2013 | Djupesland |
| 8,555,877 B2 | 10/2013 | Djupesland |
| 8,555,878 B2 | 10/2013 | Djupesland |
| 8,590,530 B2 | 11/2013 | Djupesland et al. |
| 8,596,278 B2 | 12/2013 | Djupesland |
| 8,800,555 B2 | 8/2014 | Djupesland |
| 8,875,704 B2 | 11/2014 | Djupesland et al. |
| 8,899,229 B2 | 12/2014 | Djupesland et al. |
| 8,910,629 B2 | 12/2014 | Djupesland et al. |
| D723,156 S | 2/2015 | Djupesland et al. |
| D725,769 S | 3/2015 | Djupesland et al. |
| 8,978,647 B2 | 3/2015 | Djupesland et al. |
| 9,010,325 B2 | 4/2015 | Djupesland et al. |
| 9,038,630 B2 | 5/2015 | Djupesland et al. |
| 9,067,034 B2 | 6/2015 | Djupesland et al. |
| 9,072,857 B2 | 7/2015 | Djupesland |
| 9,108,015 B2 | 8/2015 | Djupesland |
| 9,119,932 B2 | 9/2015 | Djupesland |
| 9,132,249 B2 | 9/2015 | Djupesland |
| 9,144,652 B2 | 9/2015 | Djupesland et al. |
| 9,168,341 B2 | 10/2015 | Djupesland |
| 9,205,208 B2 | 12/2015 | Djupesland |
| 9,205,209 B2 | 12/2015 | Djupesland |
| 9,272,104 B2 | 3/2016 | Djupesland |
| D759,805 S | 6/2016 | Djupesland |
| D761,951 S | 7/2016 | Djupesland |
| 9,452,272 B2 | 9/2016 | Djupesland et al. |
| 9,468,727 B2 | 10/2016 | Djupesland |
| D773,644 S | 12/2016 | Djupesland |
| 9,522,243 B2 | 12/2016 | Djupesland |
| 9,566,402 B2 | 2/2017 | Djupesland |
| 9,649,456 B2 | 5/2017 | Djupesland et al. |
| D809,128 S | 1/2018 | Djupesland |
| 9,949,923 B2 | 4/2018 | Djupesland |
| 2004/0024330 A1 | 2/2004 | Djupesland et al. |
| 2004/0112378 A1 | 6/2004 | Djupesland |
| 2004/0112379 A1 | 6/2004 | Djupesland |
| 2004/0112380 A1 | 6/2004 | Djupesland |
| 2004/0149289 A1 | 8/2004 | Djupesland |
| 2004/0182388 A1 | 9/2004 | Djupesland |
| 2005/0028812 A1 | 2/2005 | Djupesland |
| 2005/0072430 A1 | 4/2005 | Djupesland |
| 2005/0235992 A1 | 10/2005 | Djupesland |
| 2006/0096589 A1 | 5/2006 | Djupesland |
| 2006/0107957 A1 | 5/2006 | Djupesland |
| 2006/0169278 A1 | 8/2006 | Djupesland et al. |
| 2006/0219240 A1 | 10/2006 | Djupesland |
| 2006/0219241 A1 | 10/2006 | Djupesland |
| 2006/0225732 A1 | 10/2006 | Djupesland |
| 2006/0231094 A1 | 10/2006 | Djupesland |
| 2007/0039614 A1 | 2/2007 | Djupesland |
| 2007/0125371 A1 | 6/2007 | Djupesland |
| 2007/0186927 A1 | 8/2007 | Djupesland et al. |
| 2008/0161771 A1 | 7/2008 | Djupesland |
| 2008/0163874 A1 | 7/2008 | Djupesland |
| 2008/0221471 A1 | 9/2008 | Djupesland et al. |
| 2008/0223363 A1 | 9/2008 | Djupesland |
| 2008/0289629 A1 | 11/2008 | Djupesland et al. |
| 2009/0101146 A1 | 4/2009 | Djupesland |
| 2009/0293873 A1 | 12/2009 | Djupesland et al. |
| 2009/0304802 A1 | 12/2009 | Djupesland et al. |
| 2009/0314293 A1 | 12/2009 | Djupesland |
| 2009/0320832 A1 | 12/2009 | Djupesland |
| 2010/0035805 A1 | 2/2010 | Hafner |
| 2010/0051022 A1 | 3/2010 | Djupesland et al. |
| 2010/0057047 A1 | 3/2010 | Djupesland et al. |
| 2010/0199984 A1 | 8/2010 | Williams et al. |
| 2010/0242959 A1 | 9/2010 | Djupesland et al. |
| 2010/0282246 A1 | 11/2010 | Djupesland et al. |
| 2010/0288275 A1 | 11/2010 | Djupesland et al. |
| 2010/0300439 A1 | 12/2010 | Djupesland et al. |
| 2011/0023869 A1 | 2/2011 | Djupesland |
| 2011/0053827 A1 | 3/2011 | Hafner |
| 2011/0088690 A1 | 4/2011 | Djupesland et al. |
| 2011/0088691 A1 | 4/2011 | Djupesland |
| 2011/0114087 A1 | 5/2011 | Djupesland et al. |
| 2011/0120456 A1 | 5/2011 | Immel |
| 2011/0126830 A1 | 6/2011 | Djupesland et al. |
| 2011/0259329 A1 | 10/2011 | Djupesland et al. |
| 2011/0318345 A1 | 12/2011 | Djupesland |
| 2012/0000459 A1 | 1/2012 | Djupesland |
| 2012/0006323 A1 | 1/2012 | Djupesland |
| 2012/0073571 A1 | 3/2012 | Djupesland |
| 2012/0090608 A1 | 4/2012 | Djupesland et al. |
| 2012/0260915 A1 | 10/2012 | Djupesland |
| 2013/0098362 A1 | 4/2013 | Djupesland et al. |
| 2013/0125889 A1 | 5/2013 | Djupesland et al. |
| 2013/0327320 A1 | 12/2013 | Djupesland |
| 2014/0018295 A1 | 1/2014 | Djupesland |
| 2014/0041660 A1 | 2/2014 | Djupesland et al. |
| 2014/0060536 A1 | 3/2014 | Djupesland |
| 2014/0073562 A1 | 3/2014 | Djupesland |
| 2014/0144442 A1 | 5/2014 | Djupesland et al. |
| 2014/0144443 A1 | 5/2014 | Djupesland et al. |
| 2014/0166008 A1 | 6/2014 | Djupesland |
| 2014/0202456 A1 | 7/2014 | Djupesland |
| 2014/0246022 A1 | 9/2014 | Djupesland et al. |
| 2015/0007811 A1 | 1/2015 | Djupesland et al. |

(56) References Cited

U.S. PATENT DOCUMENTS

| | | |
|---|---|---|
| 2015/0013670 A1 | 1/2015 | Djupesland et al. |
| 2015/0013677 A1 | 1/2015 | Djupesland et al. |
| 2015/0053201 A1 | 2/2015 | Djupesland et al. |
| 2015/0090259 A1 | 4/2015 | Djupesland et al. |
| 2015/0101605 A1 | 4/2015 | Djupesland et al. |
| 2015/0144129 A1 | 5/2015 | Djupesland et al. |
| 2015/0165139 A1 | 6/2015 | Hafner |
| 2015/0182709 A1 | 7/2015 | Djupesland |
| 2015/0246194 A1 | 9/2015 | Djupesland et al. |
| 2015/0367090 A1 | 12/2015 | Djupesland et al. |
| 2015/0367091 A1 | 12/2015 | Djupesland et al. |
| 2016/0001022 A1 | 1/2016 | Djupesland et al. |
| 2016/0045687 A1 | 2/2016 | Djupesland |
| 2016/0051778 A1 | 2/2016 | Djupesland et al. |
| 2016/0074603 A1 | 3/2016 | Djupesland et al. |
| 2016/0082206 A1 | 3/2016 | Djupesland et al. |
| 2016/0082207 A1 | 3/2016 | Djupesland et al. |
| 2016/0095989 A1 | 4/2016 | Djupesland |
| 2016/0095993 A1 | 4/2016 | Djupesland |
| 2016/0101249 A1 | 4/2016 | Djupesland |
| 2016/0166788 A1 | 6/2016 | Djupesland et al. |
| 2016/0184571 A1 | 6/2016 | Djupesland |
| 2016/0193435 A1 | 7/2016 | Djupesland |
| 2016/0250408 A1 | 9/2016 | Djupesland |
| 2016/0263334 A1 | 9/2016 | Djupesland |
| 2016/0279357 A1 | 9/2016 | Djupesland |
| 2016/0310683 A1 | 10/2016 | Djupesland et al. |
| 2016/0331916 A1 | 11/2016 | Djupesland et al. |
| 2016/0367771 A1 | 12/2016 | Djupesland |
| 2016/0367772 A1 | 12/2016 | Djupesland |
| 2016/0367774 A1 | 12/2016 | Djupesland et al. |
| 2017/0043108 A1 | 2/2017 | Djupesland et al. |
| 2017/0151397 A1 | 6/2017 | Djupesland |
| 2017/0203061 A1 | 7/2017 | Djupesland et al. |
| 2017/0216540 A1 | 8/2017 | Djupesland |
| 2017/0274164 A1 | 9/2017 | Djupesland et al. |
| 2017/0333649 A1 | 11/2017 | Djupesland |

FOREIGN PATENT DOCUMENTS

| | | |
|---|---|---|
| GB | 2 418 147 | 3/2006 |
| WO | WO 96/22802 | 8/1996 |
| WO | WO 98/53869 | 12/1998 |
| WO | WO 00/51672 | 9/2000 |
| WO | WO 01/97689 | 12/2001 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | WO 03/000310 | 1/2003 |
| WO | WO 03/020350 | 3/2003 |
| WO | WO 03/082393 | 10/2003 |
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO 2004/060433 | 7/2004 |
| WO | WO 2004/103447 | 12/2004 |
| WO | WO 2005/016423 | 2/2005 |
| WO | WO 2005/021059 | 3/2005 |
| WO | WO 2006/030210 | 3/2006 |
| WO | WO 2006/090149 | 8/2006 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO 2008/065403 | 6/2008 |
| WO | WO 2008/081326 | 7/2008 |
| WO | WO 2008/081327 | 7/2008 |
| WO | WO 2008/122791 | 10/2008 |
| WO | WO 2008/122795 | 10/2008 |
| WO | WO 2009/044172 | 4/2009 |
| WO | WO 2010/029441 | 3/2010 |
| WO | WO 2012/035427 | 3/2012 |
| WO | WO 2012/123819 | 9/2012 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |

OTHER PUBLICATIONS

Per Gisle Djupesland, *Nasal Delivery of Vaccines*, EPC (Jan. 29, 2003).

Per Gisle Djupesland, *Who Nose How Far Nasal Delivery Can Go?*, EPC (Oct. 7, 2003).

Per Gisle Djupesland, *Bi-directional Nasal Drug Delivery*, Innovations in Pharmaceutical Technology (Jul. 10, 2004).

P.G. Djupesland, *Bi-Directional Nasal Delivery of Aerosols Can Prevent Lung Deposition*, Journal of Aerosol Medicine (Sep. 2004).

*Bi-Directional Nasal Device Delivers Drug on Exhalation*, Pharmaceutical Technology (Sep. 10, 2004).

Ola Dale et al., *Intranasal Midazolam: A Comparison of Two Delivery Devices in Human Volunteers*, Journal of Pharmacy and Pharmacology (Oct. 2004).

G. Furness, *Nasal Drug Delivery: Rapid Onset Via a Convenient Route*, ONdrugDelivery Ltd. (2005).

M. Kleven, *Using Computational Fluid Dynamics (CFD) to Improve the Bi-Directional Nasal Drug Delivery Concept*, Trans IChemE Part C. (Jun. 2005).

Per Gisle Djupesland, *Breath-Actuated Bi-Directional Delivery Sets the Nasal Market on a New Course*, ONdrugDelivery (Oct. 10, 2005).

Hilde Bakke et al., *Oral Spray Immunization May be an Alternative to Intranasal Vaccine Delivery to Induce Systemic Antibodies But Not Nasal Mucosal or Cellular Immunity*, Scan J. of Immunol. (Mar. 2006).

P.G. Djupesland et al., *Breath Actuated Nasal Device Improves Delivery to Target Sites Beyond the Nasal Valve*, The Laryngoscope (Mar. 2006).

R. Luthringer et al., *Rapid Absorption of Sumatriptan Powder and Effects on Glyceryl tinitrate Model of Headache Following Intranasal Delivery Using a Novel Bi-Directional Device*, Journal of Pharmacy and Pharmacology (Jan. 2009).

A. Skretting et al., *A New Method for Scintigraphic Quantification of Deposition and Clearance in Anatomical Regions of the Human Nose*, Nuclear Medicine Communications (Aug. 2009).

Vlckovia et al., *Effective Treatment of Mild-to-Moderate Nasal Polyposis with Fluticasone Delivered by a Novel Device*, Rhinology (Oct. 22, 2009).

Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).

P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).

F.S. Hansen et al., *Preliminary Efficacy of Fluticasone Delivered by a Novel Device in Recalcitrant Chronic Rhinosinusitis*, Rhinology (Jun. 26, 2010).

Per Gisle Djupesland, *Nasal Drug Delivery Devices: Characteristics and Performance in Clinical Perspective—A Review*, Drug. Deliv. and Transl. Res. (Oct. 18, 2012).

Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).

Stewart J. Tepper, *Clinical Implications for Breath-Powered Powder Sumatriptan Intranasal Treatment*, Headache, The American Headache Society (Apr. 29, 2013).

Mohammad Obaidi et al., *Improved Pharmacokinetics of Sumatriptan With Breath Powered Nasal Delivery of Sumatriptan Powder*, Headache, The American Headache Society (May 24, 2013).

(56) References Cited

OTHER PUBLICATIONS

Per Gisle Djupesland, *Breath Powdered Nasal Delivery: A New Route to Rapid Headache Relief*, Headache, The American Headache Society (Jun. 4, 2013).

Per Gisle Djupesland et al., *The Nasal Approach to Delivering Treatment for Brain Diseases: An Anatomic, Physiologic, and Delivery Technology Overview*, Therapeutic Delivery (2014).

R.K. Cady et al., *A Randomized Double-Blind, Placebo Controlled Study of Breath Powered Nasal Delivery of Sumatriptan Powder (AVP-825) in the Treatment of Acute Migraine (The Target Study)*, Headache (Sep. 8, 2014).

S.J. Tepper et al., *AVP-825 Breath-Powdered Intranasal Delivery System Containing 22 mg Sumatriptan Powder vs. 100 mg Oral Sumatripta in the Acute Treatment of Migraines (The Compass Study): A Comparative Randomized Clinical Trial Across Multiple Attacks*, Headache: The Journal of Head and Face Pain (Mar. 29, 2015).

D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).

R. Mahmoud, *Breathe Out*, Innovations in Phar, Tech. (Dec. 10, 2015).

DELIVERY DEVICES

This application is a continuation application of U.S. application Ser. No. 15/133,356, filed on Apr. 20, 2016, which is a continuation application of U.S. application Ser. No. 14/171,554, filed on Feb. 3, 2014, now abandoned, which is a continuation application of U.S. application Ser. No. 12/516,401, filed on Jul. 12, 2010, now abandoned, which is a U.S. national phase application of International Application No. PCT/IB2007/004353, filed on Nov. 28, 2007, which claims priority to GB Application No. 0623731.7, filed on Nov. 28, 2006. The disclosure of each of the above applications is incorporated herein by reference in its entirety.

The present invention relates to a delivery device for and method of delivering a metered volume of substance, in particular a delivery device for delivering a metered volume of a liquid substance to a nasal cavity of a subject.

Very many delivery devices exist for the delivery of liquid substances, which typically comprise a manually-actuated pump for the delivery of a liquid substance as an aerosol spray.

Whilst these delivery devices have found extensive application, the present inventors have recognized the need for a delivery device which utilizes the exhalation breath of a user as the driving force to deliver a metered dose of a liquid substance.

In one aspect the present invention provides a delivery device for delivering a metered amount of substance in response to exhalation by a user, the delivery device comprising: a mouthpiece through which the user in use exhales; an outlet from which substance is delivered; and a dispensing unit which is operable to dispense a metered amount of substance through the outlet in response to exhalation by the user through the mouthpiece, wherein the dispensing unit comprises a body member which includes a cavity for containing a metered amount of substance, an outlet nozzle which is fluidly connected to the cavity from which substance is in use delivered, and a dispensing member which is movably disposed in the cavity and configured to be driven through the cavity by a driving pressure created by exhalation of the user, such as to cause substance to be delivered from the outlet nozzle.

In one embodiment the cavity is an elongate cavity.

In one embodiment the cavity has a cylindrical section and the dispensing member comprises a ball which is moved along the cavity by the driving pressure created by exhalation of the user.

In one embodiment the ball sealingly engages with an inner peripheral wall of the cavity.

In one embodiment the cavity and the dispensing member are configured to provide for movement of the dispensing member at a driving pressure of less than about 5 kPa, and preferably less than about 3 kPa.

In one embodiment the outlet nozzle provides for an aerosol spray.

In one embodiment the outlet nozzle provides for a substantially rectilinear flow for a distance of at least about 15 mm, preferably at least about 20 mm, more preferably at least about 25 mm and yet more preferably at least about 30 mm from exit of the outlet nozzle.

In another embodiment the outlet nozzle provides for a jet.

In one embodiment the delivery device further comprises: a pressure regulator which is fluidly connected to the dispensing unit, such as to provide for application of a predeterminable driving pressure to the dispensing member.

In one embodiment the mouthpiece and the outlet are fluidly connected, such as to provide for an air flow through the outlet on exhalation by the user through the mouthpiece.

In one embodiment the delivery device further comprises: a housing in which the dispensing unit is disposed and to which the mouthpiece and the nosepiece are fluidly connected, such as to define a fluid communication path therebetween.

In one embodiment the delivery device further comprises: a baffle member which is disposed in the fluid communication path.

In one embodiment the baffle member includes a first, driving air pressure channel which is fluidly connected to the dispensing unit and at which the driving pressure is created on exhalation by the user to actuate the dispensing unit, and at least one second, entraining air flow channel through which an entraining air flow is delivered for entraining substance as delivered by the dispensing unit.

In one embodiment the baffle member includes a plurality of entraining air flow channels.

In one embodiment the housing includes an inlet chamber upstream of the baffle member which flares outwardly from the mouthpiece.

In one embodiment the housing includes an outlet chamber downstream of the baffle member.

In one embodiment the outlet chamber surrounds the dispensing unit.

In one embodiment the outlet includes a flow restrictor for providing a flow restriction thereat.

In one embodiment the flow restrictor tapers inwardly in a flow direction from the mouthpiece to the nosepiece.

In one embodiment the flow restrictor has a frusto-conical section.

In one embodiment the delivery device further comprises: a flow regulator which is disposed at the outlet nozzle of the dispensing unit.

In one embodiment the flow regulator includes a plurality of flow apertures which are located on an annulus surrounding the outlet nozzle.

In one embodiment the delivery device is configured to deliver a liquid.

In one embodiment the outlet is a nosepiece and the delivery device is a nasal delivery device for delivering substance to a nasal airway of a subject.

A preferred embodiment of the present invention will now be described hereinbelow by way of example only with reference to the accompanying drawings, in which.

Figure 1:
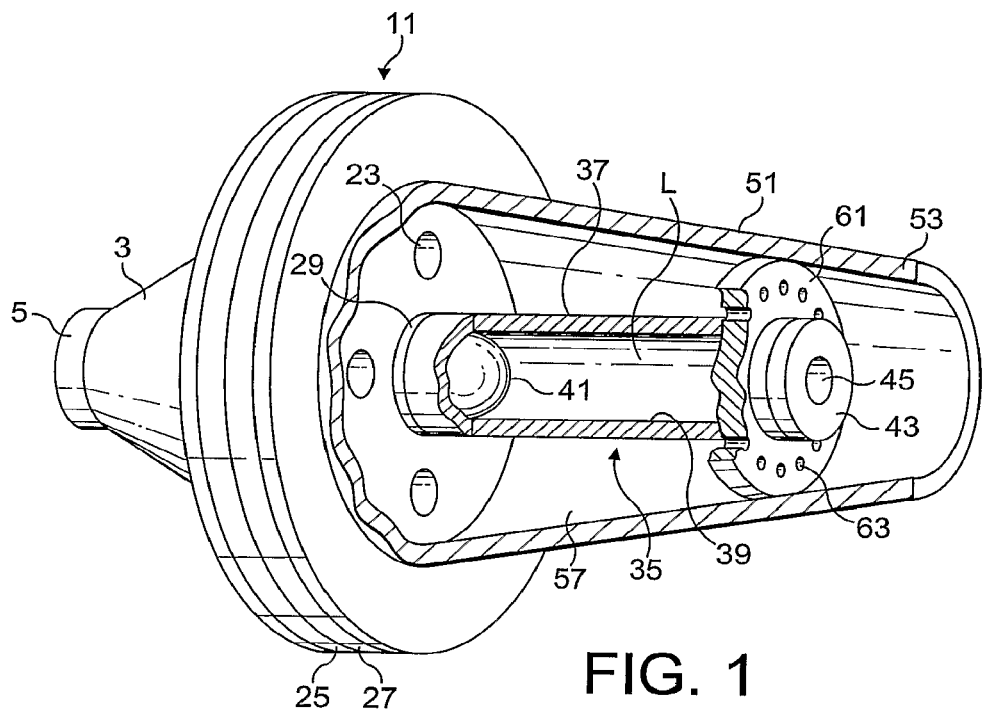
FIG. 1 illustrates a part-sectional perspective view of a delivery device in accordance with a preferred embodiment of the present invention.
Figure 2:
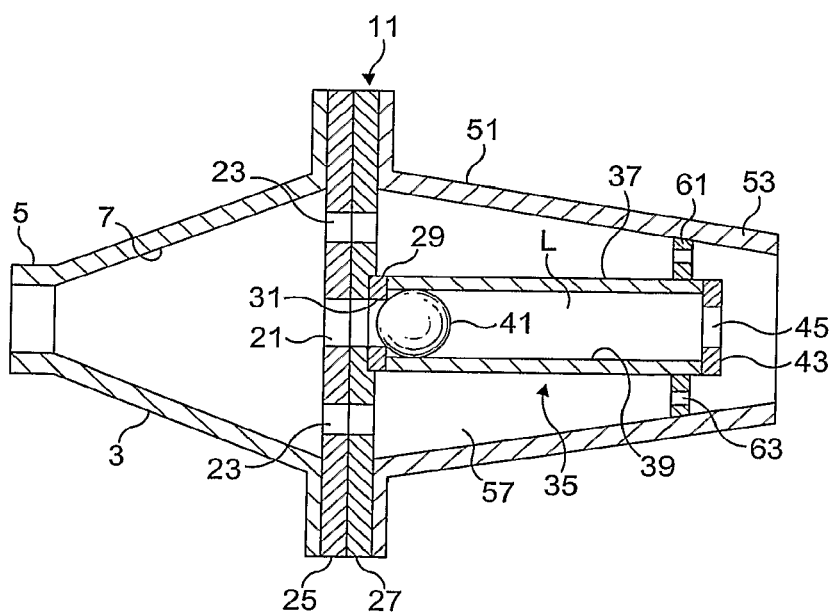
FIG. 2 illustrates a longitudinal sectional view of the delivery device of FIG. 1, where in the rest or non-actuated state.
Figure 3:
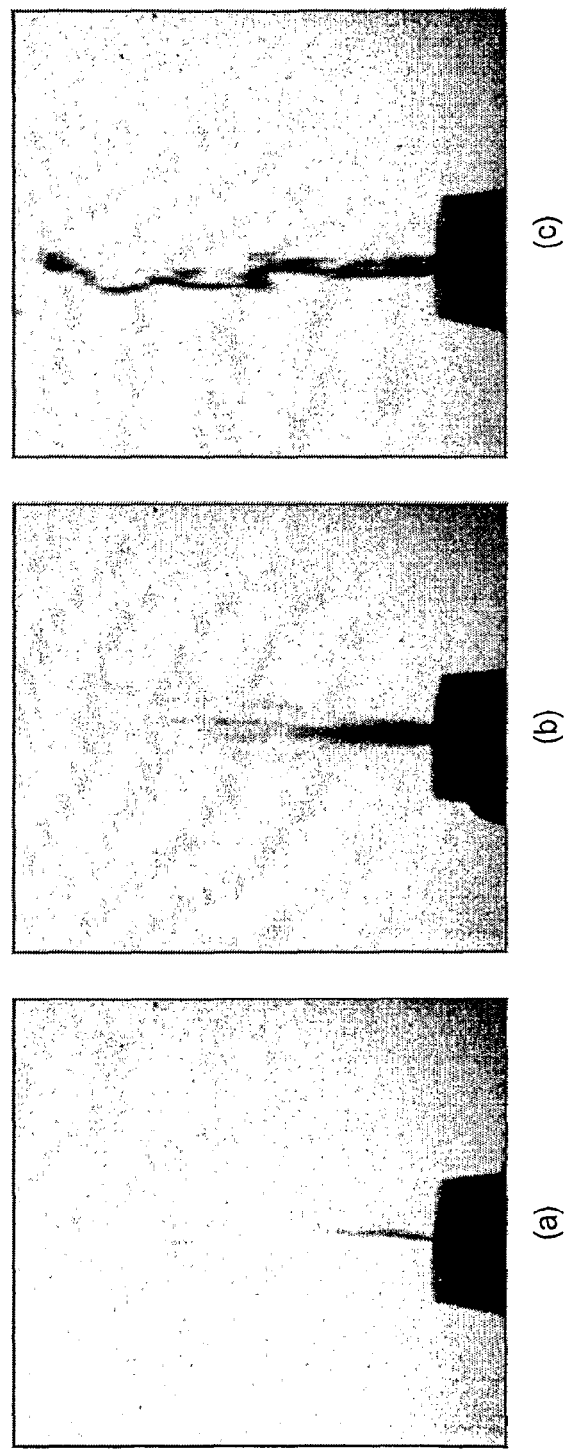
Figure 4:
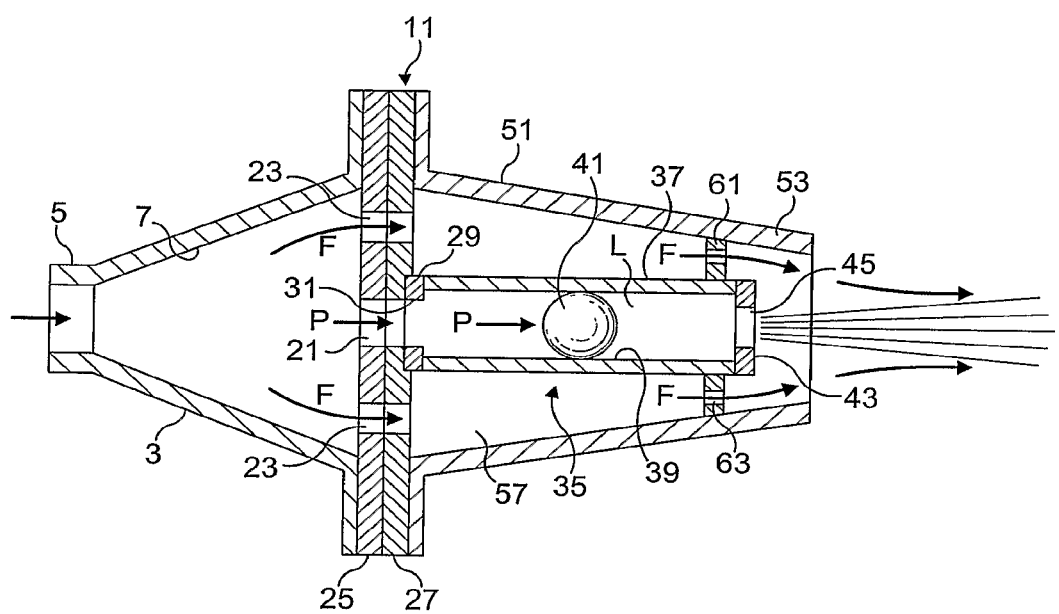
Figure 5:
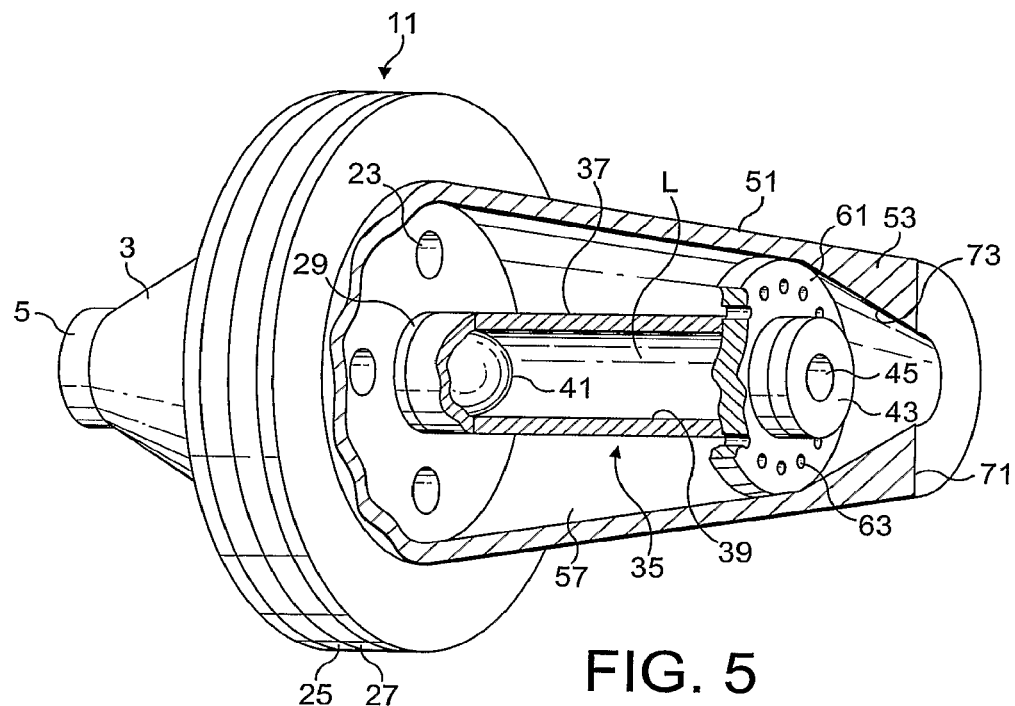
Figure 6:
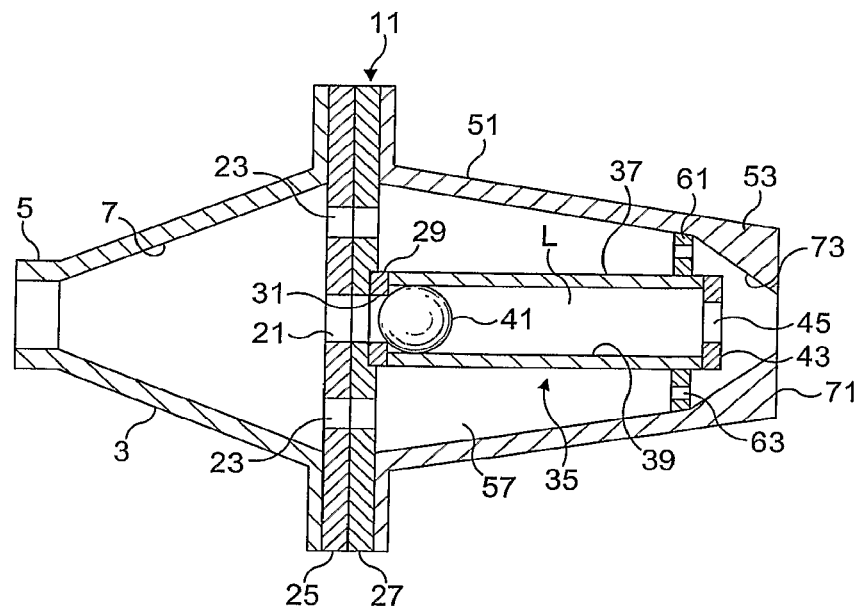

FIGS. 3(a) to (c) illustrate three delivery profiles for the delivered substance obtainable by the delivery device of FIG. 1;

FIG. 4 illustrates the delivery device of FIG. 1, where in the actuated state;

FIG. 5 illustrates a part-sectional perspective view of a delivery device as a modification of the delivery device of FIG. 1; and FIG. 6 illustrates a longitudinal sectional view of the delivery device of FIG. 5.

The delivery device comprises a first, inlet housing part 3 which defines a mouthpiece 5 at one, inlet end thereof and an inlet chamber 7 which is in fluid communication with the mouthpiece 5 and the other, outlet end of which is open, such that exhalation by a user into the mouthpiece 5 delivers an air flow into the inlet chamber 7 and to the open, outlet end thereof.

In this embodiment the mouthpiece 5 comprises a tubular section which is gripped in the lips of the user.

In this embodiment the inlet chamber 7 flares outwardly from the mouthpiece 5, here having a frusto-conical section.

The delivery device further comprises a baffle member 11 which sealingly engages the open, outlet end of the inlet chamber 7, such as to direct the air flow as delivered through the inlet chamber 7.

The baffle member 11 includes a first, driving air pressure channel 21 at which a driving pressure is created, which acts to drive a liquid dispensing unit 35, as will be described in more detail hereinbelow, and at least one, in this embodiment a plurality of second, entraining air flow channels 23 through which an entraining air flow F is delivered.

In this embodiment the first, driving air pressure channel 21 is located on the longitudinal axis of the inlet chamber 7. In this embodiment the driving air pressure channel 21 has a circular section, here having a diameter of at or less than about 6 mm.

In this embodiment the entraining air flow channels 23 are located such as to be in fluid communication with the periphery of the open, outlet end of the inlet chamber 7. In this embodiment the baffle member 11 includes four entraining air flow channels 23 which are disposed uniformly on an annulus about the longitudinal axis of the inlet housing part 3, and each have a circular section, here having a diameter of at or less than about 4 mm.

In this embodiment the baffle member 11 comprises first and second baffle elements 25, 27, here plates which are disposed in juxtaposed relation.

The delivery device further comprises a pressure regulator 29 which includes an aperture 31 which is fluidly connected to the driving air pressure channel 21 in the baffle member 11, in this embodiment at the downstream end thereof, such as to provide for the generation of a predetermined pressure thereat. In this embodiment the aperture 31 has a circular section, here having a diameter of at or less than about 4 mm.

The delivery device further comprises a liquid dispensing unit 35 which is fluidly connected to the pressure regulator 29 such as to be actuated by the driving air pressure P as generated on exhalation by the user through the mouthpiece 5.

The liquid dispensing unit 35 comprises a body member 37, in this embodiment a tubular member, here of cylindrical section, which defines an elongate cavity 39 which contains a metered dose of a liquid L, a dispensing member 41 which is movably disposed in the cavity 39, such as to be moved along the cavity 39 under the action of the driving air pressure P and thereby dispense the liquid L from the cavity 39, and an outlet nozzle 43 which is configured to provide for dispensing of the liquid L at a predetermined rate.

In this embodiment the cavity 39 has a volume of about 1 ml. In another embodiment the cavity 39 could have a volume of or less than about 200 μl.

In this embodiment the dispensing member 41 is initially disposed at one end of the cavity 39 adjacent the flow regulator 29 and is moved to the other end of the cavity 39 under the action of the driving air pressure, with the liquid L as contained in the cavity 39 being progressively dispensed as the dispensing member 41 is moved along the cavity 39.

In this embodiment the dispensing member 41 and the cavity 39 of the liquid dispensing unit 35 are configured to provide for movement with a driving air pressure P at or less than about 5 kPa and preferably at or less than about 3 kPa.

In this embodiment the dispensing member 41 is a ball which sealingly engages the peripheral wall of the cavity 39.

The outlet nozzle 43 includes an outlet orifice 45 which is shaped and dimensioned, in this embodiment having a circular section, to provide the dispensed liquid with a predetermined profile. In this embodiment the outlet orifice 45 is configured to dispense the liquid L such that the flow of liquid L remains substantially rectilinear for a distance of at least about 15 mm, preferably at least about 20 mm, more preferably at least about 25 mm and yet more preferably at least about 30 mm from the exit of the outlet orifice 45 and thereafter provide a dispersed aerosol spray, as illustrated in FIG. 3(*a*). In an alternative embodiment the outlet orifice 45 can be configured to provide a liquid jet, either with some dispersion in the form of a shower of droplets, as illustrated in FIG. 3(*b*), or with no dispersion, as illustrated in FIG. 3(*c*).

In preferred embodiments the outlet orifice 45 has a diameter of at or less than about 3 mm, preferably at or less than about 2 mm, and more preferably at or less than about 1 mm.

In this embodiment the outlet nozzle 43 includes a frangible membrane which normally encloses the outlet orifice 45 thereof such as to contain the liquid L and is ruptured on the application of the driving air pressure P to the liquid L.

The delivery device further comprises a second, outlet housing part 51 which defines a nosepiece 53 at one, outlet end thereof and an outlet chamber 57, in this embodiment an annular chamber surrounding the body member 37 of the liquid dispensing unit 35, which is in fluid communication with the entraining air flow channels 23 in the baffle member 11 and opens to an outlet end thereof, such that exhalation by a user into the mouthpiece 5 delivers an entraining air flow F into the outlet chamber 57 and to the open, outlet end thereof.

The delivery device further comprises a flow regulator 61 which encloses the annular outlet chamber 57 at the outlet end of the body member 37 of the liquid dispensing unit 35.

In this embodiment the flow regulator 61 includes a plurality of flow apertures 63, in this embodiment sixteen apertures, which are located on an annulus surrounding the body member 37 of the liquid dispensing unit 35, such as to provide for the delivery of a substantially annular entraining air flow F which entrains the liquid L as dispensed from the liquid-containing cavity 39 of the liquid dispensing unit 35.

In this embodiment the flow regulator 61 is configured to provide for a flow rate of at least about 20 l/min, more preferably at least about 30 l/min, still more preferably at least about 40 l/min and yet more preferably at least about 50 l/min.

In this embodiment the flow apertures 63 have a circular section, here of a diameter of at or less than about 1 mm.

Operation of the above-described delivery device will now be described hereinbelow with reference to FIG. 4 of the accompanying drawings.

A user first inserts the nosepiece 53 into one of his/her nostrils and then grips the mouthpiece 5 in his/her lips. It should be understood that, for the sake of ease of illustration, the delivery device has been illustrated in an elongate configuration where the nosepiece 53 and the mouthpiece 5 are located on a common axis. In practice, the nosepiece 53 and the mouthpiece 5 would be inclined relative to one another, such as to facilitate fitting of the nosepiece 53 and the mouthpiece 5 in respective ones of a nostril and the lips.

The user then exhales through the mouthpiece 5, which is in fluid communication with the inlet chamber 7.

This exhalation acts to generate a driving air pressure P at the driving air pressure channel 21 in the baffle member 11 and an entraining air flow F through the entraining air flow channels 23 in the baffle member 11, which entraining air flow F continues through the outlet chamber 57 and the flow apertures 63 in the entraining air flow regulator 61, which define a substantially annular entraining air flow F which surrounds the outlet end of the liquid dispensing unit 35.

The driving air pressure P as created at the driving air pressure channel 21 simultaneously acts on the dispensing member 41, which is located in the cavity 39 of the liquid dispensing unit 35, such as to move the same along the cavity 39 and dispense the liquid L as contained therein from the outlet end thereof into the entraining air flow F, which surrounds the same, thereby providing for delivery of the liquid L, in this embodiment into the nasal cavity of the user.

In this embodiment the delivery device, in providing for the delivery of the liquid L in an entraining air flow F, advantageously provides for delivery into and through the nasal airway in the manner as described in the applicant's earlier WO-A-2000/051672, the content of which is herein incorporated by reference.

Finally, it will be understood that the present invention has been described in its preferred embodiment and can be modified in many different ways without departing from the scope of the invention as defined by the appended claims.

In one modification, as illustrated in FIGS. 5 and 6, the delivery device can further comprise a flow restrictor 71 at the outlet end of the outlet housing part 51 which defines the nosepiece 53. In this embodiment the flow restrictor 71 tapers inwardly, here with a frusto-conical section 73, towards the outlet end of the outlet housing part 51. In this embodiment the flow restrictor 71 defines an outlet which has a circular section. In preferred embodiments the outlet of the flow restrictor 71 has a diameter of at or less than about 8 mm, preferably at or less than about 6 mm and more preferably at or less than about 4 mm, and the angle of the tapering section 73 of the flow restrictor 71 has an angle of at or less than about 60 degrees, preferably at or less than about 55 degrees and more preferably at or less than about 52 degrees relative to a plane perpendicular to the longitudinal axis of the outlet housing part 51. With this configuration, a faster delivery of the liquid L can be achieved as compared to the above-described embodiment.

The invention claimed is:

1. A delivery device for delivering a substance in response to exhalation by a user, the delivery device comprising:
    a mouthpiece adapted for the user to exhale through;
    an outlet from which the substance is delivered; and
    a dispensing unit operable to dispense a metered amount of the substance through the outlet in response to exhalation by the user through the mouthpiece, wherein the dispensing unit comprises a body member, the body member including a cavity containing the substance, an outlet nozzle fluidly connected to the cavity from which the substance is delivered, and a dispensing member movably disposed in the cavity and configured to be driven through the cavity by a driving pressure created by the exhalation of the user, causing the metered amount of the substance to be delivered from the outlet nozzle;
    whereby the exhalation by the user creates an exhalation flow adapted to directly act on the dispensing member.

2. The delivery device of claim 1, wherein the cavity is an elongate cavity.

3. The delivery device of claim 2, wherein the cavity has a cylindrical section and the dispensing member comprises a ball.

4. The delivery device of claim 3, wherein the ball sealingly engages an inner peripheral wall of the cavity.

5. The delivery device of claim 1, wherein the dispensing member is configured to move within the cavity when the driving pressure is less than 5 kPa.

6. The delivery device of claim 1, wherein the outlet nozzle is configured to deliver an aerosol spray.

7. The delivery device of claim 6, wherein the outlet nozzle provides for a rectilinear flow for a distance of at least 30 mm from an exit of the outlet nozzle.

8. The delivery device of claim 1, wherein the outlet nozzle is configured to deliver a jet.

9. The delivery device of claim 1, further comprising a pressure regulator fluidly connected to the dispensing unit and configured to apply a predeterminable driving pressure to the dispensing member.

10. The delivery device of claim 1, further comprising a housing defining a fluid communication path between the mouthpiece and the outlet.

11. The delivery device of claim 10, further comprising a baffle member disposed in the fluid communication path.

12. The delivery device of claim 11, wherein the baffle member includes a first, driving air pressure channel fluidly connected to the dispensing unit and at least one second, entraining air flow channel fluidly connected to the mouthpiece through which an entraining air flow is delivered for entraining the substance as delivered by the dispensing unit.

13. The delivery device of claim 12, wherein the baffle member includes a plurality of entraining air flow channels.

14. The delivery device of claim 11, wherein the housing includes an inlet chamber upstream of the baffle member and downstream of the mouthpiece which flares outwardly from the mouthpiece toward the baffle member.

15. The delivery device of claim 11, wherein the housing includes an outlet chamber downstream of the baffle member.

16. The delivery device of claim 15, wherein the outlet chamber surrounds the dispensing unit.

17. The delivery device of claim 16, further comprising:
    an annulus surrounding the outlet nozzle of the dispensing unit and positioned radially between the dispensing unit and the housing.

18. The delivery device of claim 17, wherein the annulus includes a plurality of flow apertures.

19. The delivery device of claim 1, wherein the outlet includes a flow restrictor.

20. The delivery device of claim 19, wherein the flow restrictor tapers inwardly.

21. The delivery device of claim 20, wherein the flow restrictor has a frusto-conical section.

22. The delivery device of claim 1, where the delivery device is configured to deliver a liquid.

23. The delivery device of claim 1, wherein the outlet is a nosepiece and the delivery device is a nasal delivery device for delivering the substance to a nasal airway of the user.

* * * * *